United States Patent [19]

Heyser et al.

[11] 4,083,232

[45] Apr. 11, 1978

[54] MEDICAL TOMOGRAPH SYSTEM USING ULTRASONIC TRANSMISSION

[75] Inventors: Richard C. Heyser, Tujunga; Robert Nathan, Pasadena, both of Calif.

[73] Assignee: California Institute of Technology, Pasadena, Calif.

[21] Appl. No.: 679,732

[22] Filed: Apr. 23, 1976

[51] Int. Cl.[2] .......................................... G01N 29/00
[52] U.S. Cl. ..................................... 73/599; 73/619; 73/624
[58] Field of Search .................. 73/67.5 R, 67.6, 67.7, 73/67.8 R, 67.8 S

[56] References Cited

U.S. PATENT DOCUMENTS 3,778,614  12/1973  Hounsfield .................. 73/67.5 R X
3,856,985  12/1974  Yokoi et al. .................. 73/67.8 S X
3,864,661  2/1975  Ranalli .......................... 73/67.7 X Primary Examiner—Jerry W. Myracle
Attorney, Agent, or Firm—Lindenberg, Freilich, Hornbaker, Wasserman, Rosen & Fernandez

[57] ABSTRACT

Ultrasonic energy transmission in rectilinear array scanning patterns of soft tissue provides projection density values of the tissue which are recorded as a function of scanning position and angular relationship, $\theta$, of the subject with a fixed coordinate system. A plurality of rectilinear scan arrays in the same plane for different angular relationships $\theta_1 \ldots \theta_n$ thus recorded are superimposed. The superimposition of intensity values thus yields a tomographic image of an internal section of the tissue in the scanning plane.

10 Claims, 4 Drawing Figures

TOMOGRAPHIC SECTION OF SPECIMEN OR BODY

MEDICAL TOMOGRAPH SYSTEM USING ULTRASONIC TRANSMISSION

ORIGIN OF THE INVENTION

The invention described herein was made in the performance of work under a NASA contract and is subject to the provisions of Section 305 of the National Aeronautics and Space Act of 1958, Public Law 85–568 (72 Stat. 435; 42 USC 2457).

BACKGROUND OF THE INVENTION

This invention relates to a method and apparatus for imaging an internal section (planar slice) through a specimen of tissue, and particularly to tomographic imaging of a section of soft tissue in vitro or in vivo.

A great deal of attention has been given recently to a medical tomographic reconstruction technique for X-rays known as computerized axial tomography (CAT). The first usable system was designed for making tomographs of the head. Although of relatively low resolution (about 3 mm as compared to 0.2 mm for the conventional X-ray shadowgram), that system has produced significant additional information for X-ray diagnosis since it recovers information which would otherwise be lost by integration in the shadowgram. Another well-known diagnostic technique, that of pulse-echo ultrasonics, also produces an image. In this case, however, the image is created by brightening a CRT screen at a position corresponding to a reflecting tissue interface in the body. The result is thus not a tomographic image.

In a recent paper, "Algebraic Reconstruction of Spatial Distributions of Acoustic Absorption within Tissue from Their Two-Dimensional Acoustic Projections," *Acoustical Holography*, Vol. 5. Plenum Press, New York, 1974, pp. 591–603, Greenleaf, et al. describe an attempt to produce a tomographic image from individual acoustical attenuation measurements using pulsed ultrasonics in the transmission mode and the computerized algebraic reconstruction technique (ART). This is an ultrasonic analog of the CAT method. The ART method was not wholly successful because of refraction and reflection of sound which interfered with the computer reconstruction and prevented an accurate tomograph from being achieved.

Traditionally, the word tomograph has referred to an X-ray picture of a selected plane section of a solid object. The advent of ultrasonic imaging using pulse-echo techniques led to a format that was geometrically identical to the X-ray tomograph in the choice of coordinates, but was an image of ultrasound reflection properties and not those of electromagnetic absorption. By convention, this type of image came to be known as an ultrasonic tomograph.

Up to the present time, this duplication of terminology could cause no confusion because of the different techniques involved (reflection vis-a-vis absorption). However, the recent introduction of image reconstruction methods capable of generating a sectional view from transilluminated projections may become a source of some confusion, particularly in the case of ultrasonic systems. (The prefix "trans-" as used herein indicates illumination through rather than over an object.) This is because there are now three basic types of tomographic images; one using X-rays and two using ultrasonics. A fourth type utilizing radioisotopes as, for example, described by Budinger, et al., "Three-Dimensional Reconstruction in Nuclear Medicine Emission Imaging," *IEE Transactions on Nuclear Science*, Vol. NS-21, pp. 2–20, 1974, is sufficiently different as to not warrant discussion. The information contained within these images is complementary. With very few exceptions, the images will show different information. One is not a replacement for the other.

The differences among the three tomographs may be seen by inspecting the three images of the same section of the body. One of these will be a conventional X-ray tomograph, and will show the differential attenuation of tissue for X-rays passing through that tissue. The second will be a conventional ultra-sonic pulse-echo tomograph, and will outline the boundaries between tissue of different acoustic impedance by indicating the amount of sound reflected back from those boundaries. The third, to which the present invention pertains, will be an ultrasonic tomograph made by reconstructing the information obtained by the passage of ultrasonic energy completely through the section. The information is the differential attenuation of sound through different types of tissue.

With the exception of the external boundaries of the subject and a few dominant structural characteristics, these three types of tomographs probably will not look alike. This is not to imply that any one is better than another, but rather to imply that the kind of information contained within them is diffferent. Each type of tomograph can reveal a great deal of information to someone experienced in interpreting that particular type of image. What is potentially more significant, however, is the synergism that may occur with two or three types of tomograph, each revealing its own perculiar set of information. This could lead to a diagnostic capability not available from the use of any single type of tomograph.

The class of tomograph to which this invention pertains is that obtained from a measure of the ultrasonic energy that passes completely through the tissue. This is an ultrasonic attenuation (or transmission) tomograph and, in only a general sense, is the acoustic analog of the X-ray tomograph. Because of the more complete control and processing that can take place with ultrasound signals, a great deal more relative information is obtained from this type of ultrasonic tomograph than is obtained from X-ray tomographs alone.

It is anticipated, as an example, that the attenuation ultrasonic tomograph will be particularly useful in detecting tissue lesions. In the case of scirrhous carcinoma in the breast, the tumor mass boundary is somewhat difficult to ascertain by echo ultrasonic tomography but an attenuation tomographic image should be able to show the carcinoma. Differentiation between the carcinoma and the surrounding reactive fibrous tissues should be achievable if there is a difference in absorption between the two regions. It is further anticipated that an attenuation tomograph will show differences between cystic and solid masses, which are not readily available from a reflection tomograph. The fact that ultrasonic transmission images can be made through obliquely oriented tissue boundaries, whereas echo systems must have the ultrasonic beam perpendicular to more boundaries in order for them to be seen, indicates that the continuous demarcation between different tissues will be a distinguishing feature of attenuation tomography.

On the other hand, it has to be recognized that there are some fundamental difficulties in the passage of ultrasound through the body that will always set a limit on the applicability of attenuation tomography. These limitations are those set by the phenomena of refraction, reflection, scattering absorption and dispersion of ultrasound in body tissues. To date, the only practical method of overcoming any of these limitations has been the use of pulse-echo ranging and imaging. The concepts of time delay spectrometry (TDS) described in U.S. Pat. No. 3,466,652, which will be discussed in detail hereinafter, provides the present inventors with a powerful technique enabling them to overcome some of these limitations. The technique has been shown to yield ultrasonic projection shadowgraphs (attenuation images) approaching the theoretical limit (about 1.5 mm) for the system described in a paper by Heyser (supra). The present invention utilizes that existing system, and modifications of that system produce ultrasonic attenuation tomographs.

OBJECTS AND SUMMARY OF THE INVENTION

An object of this invention is to provide a unique transmission system which substantially eliminates the aberrating effects of reflection and refraction for a substantially improved transillumination tomographic image reconstruction.

Another object is to provide instrumentation to produce a transillumination tomograph capable of showing details of the attenuation of different types of soft tissue with high resolution.

These and other objects of the invention are achieved by transmitting energy through a body in rectilinear scanning array patterns, detecting the attenuation of energy by the body in each raster of the scanning pattern, and recording attenuation detected as a function of scanning position for each of a plurality of scanning arrays 1 through N, with a direction of energy propagation through the body at respective angles $\theta_1$ through $\theta_n$ about an axis of a fixed coordinate system on the body, where the axis of angular relationship is normal to the scanning plane. The data of the rectilinear scan array recorded for the different angles are then superimposed to produce a tomograph, an image of a section of the body in the scanning plane. To provide the scan array patterns, a transmitter on one side of the body and a receiver on the other side are linked by means for moving the transmitter and receiver in parallel paths in the scanning plane for each rectilinear scan array. The body is supported by means coupled to the transmitter and receiver scanning means to hold the body in a fixed position while the scanning means completes a rectilinear scan array. Additional means is provided to change the angular relationship of the body with respect to the rectilinear array scanning means through the angles $\theta_1$ through $\theta_n$, thus providing one angular relationship about an axis normal to the scanning plane for each rectilinear scan array. A time-dependent sweep is employed for each raster of the rectilinear scan array pattern to eliminate the aberrating effects of reflection and refraction of the ultrasonic or other radiation energy transmitted through the body.

In the particular case of ultrasonic radiation from the transmitter to the receiver, the time-dependent sweep is implemented by an ultrasonic signal generator repetitively swept in frequency in a linear manner from one predetermined frequency to another in response to a sweep signal generator. At the receiver, the ultrasonic signal received is mixed with the ultrasonic signal transmitted to produce a difference frequency signal proportional to the time delay through the body of the ultrasound. A narrow bandpass filter tuned to that difference frequency thus rejects all but directly transmitted ultrasound passing through the body from the transmitter to the receiver. Each point of a linear sweep is recorded in synchronism with the signal from the sweep signal generator. According to one feature of the invention, the recording system is comprised of a cathode ray tube (CRT) having a rectilinear beam scan controlled by the sweep signal for each raster of a rectilinear display scan, the rectilinear scan being angularly oriented about an axis normal to the center of the face of the CRT and synchronized with the angular orientation of the body. A photographic film superimposes each full rectilinear scan array on previous arrays, thus integrating all scan arrays by adding them virtually point by point.

The novel features that are considered characteristic of this invention are set forth with particularity in the appended claims. The invention will best be understood from the following description when read in connection with the accompanying drawings.

DESCRIPTION OF THE PREFERRED EMBODIMENTS

Figures 1, 2:
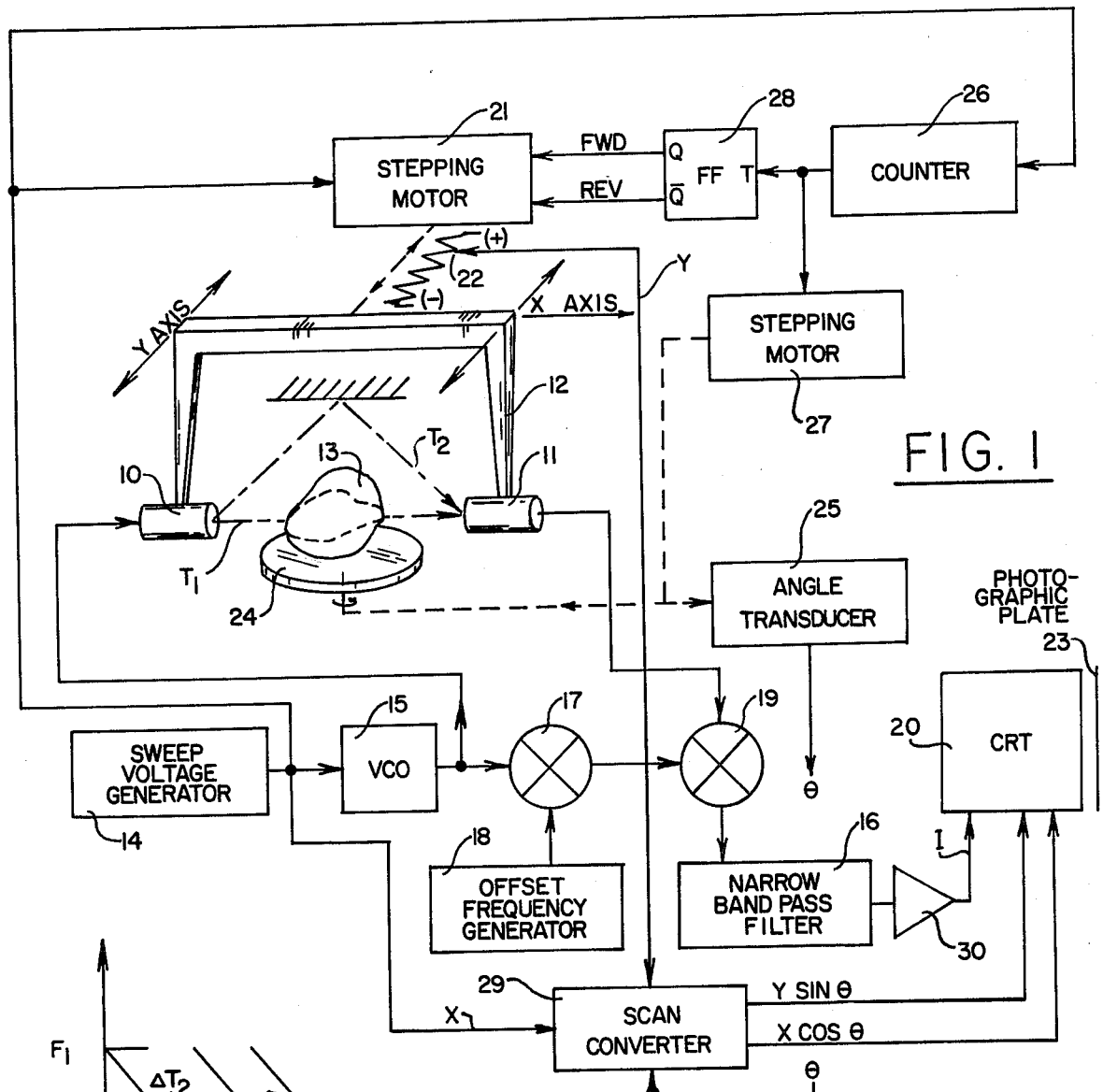
FIG. 1 is a functional block diagram of the present invention.
FIG. 2 is a graph of frequency as a function of time in a frequency sweep of a time delay spectrometer.

Referring now to the drawings, a block diagram of the system will first be described with reference to FIG. 1. Transmitting and receiving ultrasonic transducers 10 and 11 are carried by a yoke 12 for rectilinear array scanning of a specimen 13 in a plane indicated by a dotted line on the specimen.

A sweep frequency generator 14 and voltage controlled oscillator (VCO) 15 provide an ultrasound transmission of a frequency that is repetitively swept in a linear manner from frequency $F_1$ to $F_2$ as shown in a time-frequency graph in FIG. 2. At the receiving transducer 11, the signal received has the same swept frequency format, but delayed by the transmission time through the specimen.

A first signal received with a first delay time $\Delta T_1$, is one which normally travels in a direct path from the transmitting transducer to the receiving transducer. Any other signal arriving at the receiver, such as the reflected path shown in FIG. 1 with a longer delay time, $\Delta T_2$, will be at a frequency distinct from the direct signal by an amount linearly proportional to the difference in time delay, as shown in FIG. 2. This difference in frequency will permit selection of the direct-path signal to be made by a narrow bandpass filter 16. To accomplish that, the output of the sweep frequency generator is heterodyned in a mixer 17 with the output of an adjustable offset frequency generator 18 as the transmitted signal is swept in frequency.

The output of the mixer 17 is then heterodyned in a mixer 19 to produce a signal which corresponds to the direct-path signal that will pass through the narrow bandpass filter. All other signals arriving through different delay paths will fall outside the bandpass of the filter and will be rejected. In that manner the reflected path signal which incurs the greater delay, $\Delta T_2$, on its longer path to the receiving transducer will produce a heterodyned signal outside of the narrow limits of the filter and will therefore not be passed.

If the reflected signal were the one of interest, the offset frequency of the generator 18 could be increased so that, at any point in time, the output of the mixer 19 that is within the bandpass will be that of the signal delayed a greater time $\Delta T_2$. However, for the present invention the direct path signal is the one of interest. Therefore, by appropriately setting the offset generator frequency, the operator can select the direct transmission path of interest.

The minimum path difference that can be resolved is given by $$\Delta X = C/\Delta F \qquad (1)$$

where $\Delta F$ is the total swept frequency, and $C$ is the velocity of propagation. The distance traveled at velocity $C$ is represented by the vector $X_o$ in FIG. 2. The frequency offset between the transmitted signal and the direct path signal at the time of receipt is represented by the vector $F_o$ in FIG. 2. It is evident from those vectors that for a linear sweep $$X_o = F_o \frac{C}{\left(\frac{dF}{dt}\right)} \qquad (2)$$

This time-dependent transmission phenomena exploited in this manner provides a time delay spectrometer (TDS) which is more fully described in U.S. Pat. No. 3,466,652 by Richard C. Heyser.

The utilization of a TDS has some other attributes. When a linear frequency-versus-time sweep is generated, it is very simple to transfer the data between the frequency and time domains. Using oscillators with suitable phase stability, a repetitive output spectrum including both amplitude and phase is fixed by the operator, and direct measurements of the characteristics of the medium may be obtained as the sweep progresses.

What is new and provided by a TDS in the present invention is a dynamic system-testing process which breaks away from the rigid concepts of a steady-state sinewave excitation on the one hand and wide bandwidth impulse excitation on the other hand. TDS is a coherent communication process in which both the time domain and frequency domain are utilized, even if interest centers wholly on one domain. The transmitted signal discussed above has a predetermined frequency spectrum with the equivalent of a time tag to each frequency component. In the simplest case considered here, this consists of a linear frequency sweep with time in which the tag is the moment of occurrence of each frequency. Upon emergence from the specimen, the frequency components with a given time delay are reassembled to yield the frequency spectrum. Signal components due to longer path lengths, such as those caused by scattering, are effectively suppressed because their spectrum time tags reject them.

The signal displayed on a cathode ray (CRT) is the anechoic frequency response of the combined transducers and tissue path. The specific time interval represented by this frequency spectrum is separately selectable by TDS. Thus, if a multipath situation is encountered in which the desired signal is closely followed by an undesired signal which has traveled a slightly different path, it is possible to center the acceptance to TDS to the specific arrival time of interest and narrow the time window to the extent necessary to assure that the appropriate path is selected, within the limits of the experimental equipment.

Because there is a linear relationship between time and frequency, there is an easy transformation between the two domains. By using TDS, the operator has control over the range of frequencies being utilized and can thus bound the frequency range over which the measurement or analysis is carried out. The significance of this to a medical ultrasound tomograph is that TDS simultaneously yields data on the time-domain vector and frequency-domain vector that represents wave propagation through the body. In so doing, an unprecedented range and sensitivity of measurement is available for time-of-arrival measurements and their spectrum measure.

An ultrasonic transmission scanning system as discussed in Heyser, R. C. and Le Croissette, D. H., "A New Ultrasonic Imaging System Using Time Delay Spectrometry", *Ultrasound in Med. and Biol.*, Vol. 1, pp. 119–131, 1974 and Fishman, L. S., Heyser, R. C. and Le Croissette, D. H., "Ultrasonic Transmission Measurements on Human Brain Sections", *Radiology*, Vol. 112, No. 1, pp. 211–213, 1974, has been adapted to the present invention. That scanning system operates over the frequency range of 2 to 3 MHz (1 MHz sweep width). Briefly, the physical movement of the yoke in a precise raster pattern was achieved using an X-Y chart recorder mechanism driven in both the X and Y direction, and a display storage tube was used for display of the parallel rasters thus scanned.

In order to adapt the scanning system of the references cited above to the present invention, the drive mechanism in the Y axis was retained to move the yoke in one direction and thus provide an array of scan rasters in the X axis. The effective scan in the other axis (X) is achieved by synchronizing the horizontal sweep of the CRT 20 with the output of the sweep voltage generator 14 (FIG. 1). The horizontal sweep of the CRT is suitably delayed in the CRT so that each horizontal sweep is commenced when the direct path signal is received from the output of the narrow bandpass filter. The output is applied to the intensity control of the CRT. The system thus modified will provide for the imaging of a two dimensional slice. A single horizontal trace images the direct ultrasound path between the two transducers. At the end of each trace, the output of the sweep generator 14 advances a stepping motor 21, to advance the yoke to the next raster position. A transducer 22, such as a linear potentiometer, provides a Y axis signal to the CRT 20.

One array of rasters (rectilinear scans) generates only one projection recorded on a film 23. For the present invention, is it necessary to record a set of projections for various angles, $\theta$, of scan relative to fixed geometrical coordinates of the body 13. To alter the angle of scan, the specimen is fastened to a rotatable table 24 to which an angle transducer 25 is attached. A counter 26 counts the cycles of the sweep generator, and after the desired number of rasters have been scanned for one projection image, the output of the counter advances a stepping motor 27 to rotate the table 24 through some small angle (such as 7.5°). At the same time, the output of the counter triggers a T-type flip-flop 28 to reverse the directions of the stepping motor 21. In that manner one complete projection image at an angle $\theta_1$ is recorded on the film while the yoke is driven with Y axis in one direction, and a succeeding projection image at an angle $\theta_2 = \theta_1 + 7.5°$ is recorded on the film while the yoke is driven back in the opposite direction.

A scan converter 29 receives the output ($\theta$) of the angle transducer 24 and the X and Y scan signals from the sweep voltage generator 14 and transducer 22 to effectively rotate the array of rasters displayed on the CRT in synchronism with rotation of the table 24. The result is a modified C-type scan on the CRT. In the visual presentation, the coordinates of the array of rasters are thus fixed to the subject. As the table is rotated, to rotate the specimen for subsequent views, the projection image displayed and recorded is identically rotated, i.e., the X and Y axis of the CRT are effectively rotated. The reconstruction geometry on the recording film 23 is thus such that a fixed point on tomographic section corresponds to a fixed point of the specimen. However, for each projection image, i.e., for each set of rectilinear scan rasters, a given point of the specimen is being illuminated from a different angle.

Authentic reconstruction of the tomograph from a plurality of projection images is performed by the recording film (photographic plate) 23 which "adds" the spot intensity at each point from successive projection images. The basis for this is the time-exposure reciprocity known to exist over a limited range on all photographic emulsions. As an equivalent alternative, the intensity of each point in a projection image may be converted from its analog form to digital in order to use a conventional analog-to-digital converter while the X and Y coordinate signals are similarly converted to digital form. All the data thus converted to digital form is stored for later reconstruction by adding the intensities for each point of successive scan angles. The sums thus formed are then displayed on a CRT for exposure of a photographic plate.

The technique for tomographic imaging, i.e., imaging an internal plate section through a specimen by ultrasound transillumination, will now be described with reference to FIGS. 3 and 4. Other apparatus more specifically adapted to particular applications of the invention may, of course, be substituted for the exemplary apparatus which uses a CRT and photographic plate as an analog instrument for reconstruction of the tomograph. The scanning apparatus itself may also be greatly modified for the particular application, such as detecting scirrhous carcinoma in the breast. The most important applications of the present invention are expected to be in examining details of soft tissue in vivo in much the same way that X-rays are used to form tomographic images. However, it should be understood that the images formed will show different information. One is not a replacement for the other. An X-ray tomograph will show the differential attenuation of tissue for X-rays passing through that tissue. The ultrasound tomograph will show the differential attenuation for sound through various types of tissue. The type of information contained within the two tomographs is different. Each can reveal a great deal of information to a person experienced in interpreting that particular type of image. The combined information of both could lead to a diagnostic capability not available from the use of a single type of tomograph. In other words, while an X-ray tomograph gives information on the attenuation of electromagnetic radiation, an ultrasound tomograph gives information on the mechanical properties which can be correlated with the pathological status of tissue.

The ultrasonic tomographic technique is to obtain a plurality of projection images of a subject by appropriately scanning a plane section through the subject in a pattern of parallel scanning lines with a different scan angle for each projection image. The pattern is aptly referred to herein as a rectilinear scan array. The scanning lines of the array are displayed by the CRT in rasters to form a single projection image of the ultrasound attenuation experienced in the scanning lines of the array. The subject is turned to present a new view (scanning angle $\theta$) for each attenuation image. As the subject is turned, the rasters of the display are turned to provide a set of projection images for various angles of scan relative to the fixed geometrical coordinates of the subject signal values corresponding to the density of projection of each point in the plane section of the subject are added and displayed as an intensity proportional to the density values. The final record thus constituted consists of the proper tomograph plus a uniform background level which may be subtracted to enhance the tomograph.

Figure 3:
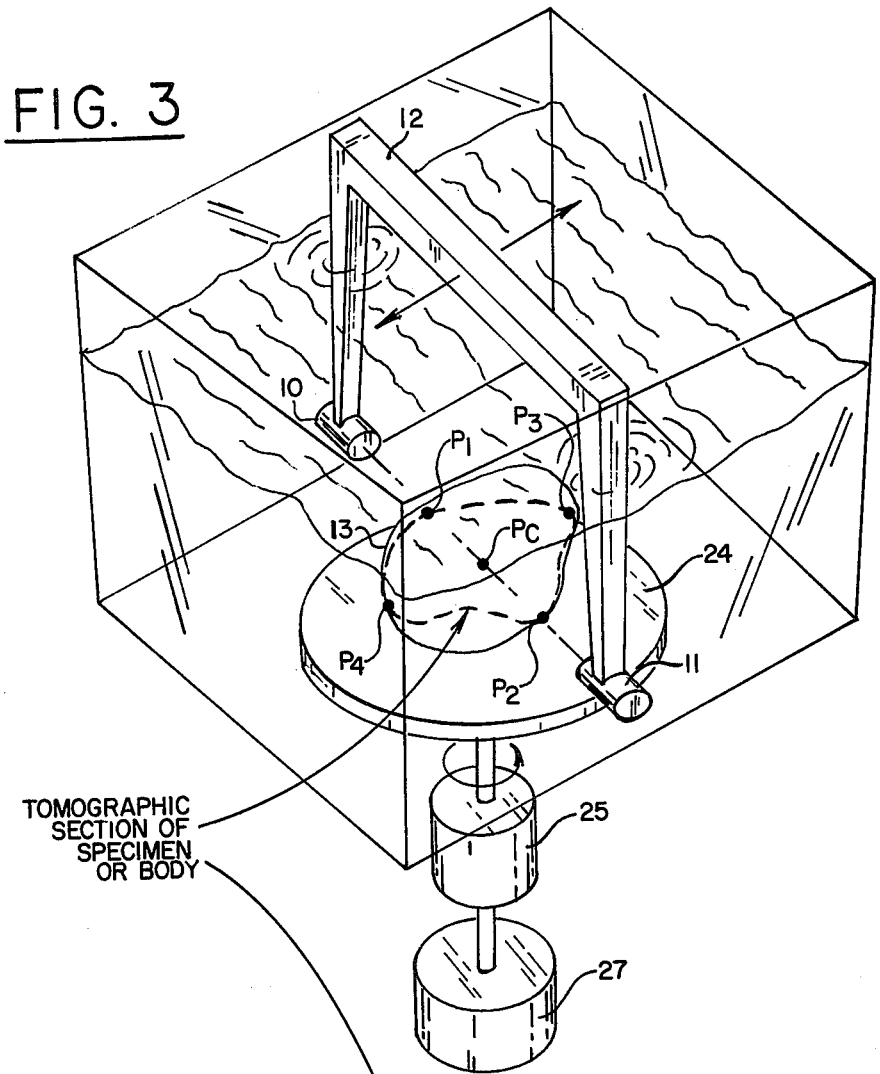
FIG. 3 is an isometric view of tomographic scanning apparatus.

To demonstrate the operation with reference to FIG. 3, the subject 13 is placed on the table 24 in a position with the desired tomographic section in the horizontal scanning plane of the transmitting and receiving transducers. The section of the subject lies wholly within a medium, such as water, that is itself structureless for ultrasonic transmission. The medium thus serves merely as an efficient coupling between the transducers and the body of the subject. The direction of propagation bears some angular relationship with fixed coordinate axes of the subject. Assuming the subject is first scanned in the position shown in FIG. 3, the fixed coordinate axes of the subject are an X axis passing through a center point $P_c$ and peripheral points $P_1$ and $P_2$, and an orthogonal Y axis passing through the center point $P_c$ and peripheral points $P_3$ and $P_4$. The scanning lines are initially parallel to the X axis and displayed on the CRT as horizontal rasters. Every point in the projection image thus corresponds to a point in the section which includes the points $P_c$, $P_1$, $P_2$, $P_3$ and $P_4$.

After the first projection image is displayed on the CRT and recorded on the photographic plate 23, the subject is rotated through an angle $\theta$. Each point in the section is thus illuminated from a different point of view and will thus be included in a different scan line. Consequently, the scan lines are not displayed on the CRT as horizontal rasters, but are instead rotated through a corresponding angle $\theta$ by the scan converter 29.

Figure 4:
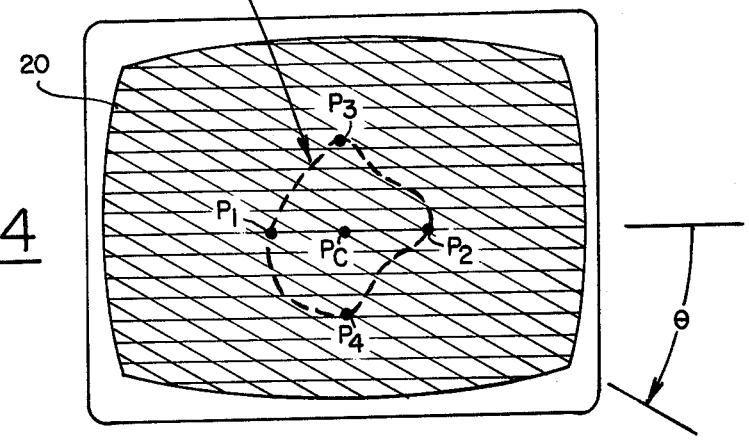
FIG. 4 illustrates the tomograph of a section scanned as viewed on a cathode ray tube.

FIG. 4 illustrates the horizontal traces of the CRT display for imaging the section with points $P_c$ and $P_1$ through $P_4$ identified. Once the subject is rotated through an angle $\theta$, the same horizontal traces of the scan lines would produce an image rotated through the angle $\theta$. It would not be possible to add the intensities at each point of the second projection image to corresponding points of the first projection image using the photographic plate if the projection image rotates through the angle $\theta$ on the CRT screen. It is for that reason that a scan converter 29 is used to rotate the display rasters through the angle $\theta$ as shown in FIG. 4 to keep the display points $P_c$ and $P_1$ through $P_4$ of the projection image fixed on the CRT. As the angle $\theta$ is increased in increments of 7.5°, a total of 48 projection images are displayed, each with the original X and Y coordinate axes coincident with the horizontal and vertical axes of the CRT with the center point $P_c$ of each image at the center of the CRT.

As each trace (raster) of each projection image is displayed, it is recorded on the photographic plate 23 (FIG. 1). Each point on the plate thus has a total exposure that is the sum of the intensities of the 48 projection images at that point. In that manner, the generation of an ultrasound tomograph uses both a linear translation and a rotation of the subject under analysis relative to the transilluminating direction. The brightness (intensity) of each scan line (raster) is made to correspond to the integrated density as measured by the TDS. Arithmetic reconstruction of the tomograph is accomplished directly by the photographic plate based on the time-exposure reciprocity known to exist over a limited range on all photographic emulsions. When self developing film is used for the photographic plate of the type used in Polaroid Land cameras, the lower end of the time-exposure scale is found to be nonlinear, thus introducing some distortion in the tomograph, but even such a distorted tomograph will be meaningful to an experienced diagnostician. However, for more accurate tomographs, the photographic plate may be more conventional photographic emulsions which are linear to a lower limit. Alternatively, the intensity output of the narrow passband filter may be converted to digital form and stored for later processing before display and recording in film, thus providing a sum for each point which will be above the nonlinear portion of the time-exposure curve of the photographic emulsion. Still another alternative is to adjust the gain of an amplifier 30 (FIG. 1) such that the minimum background energy density level is above the non-linear portion of the time-exposure curve. This raises the background level, but photographic techniques may later be used to subtract the background level.

Although a particular embodiment of the invention has been illustrated and described, it is recognized that modifications and variations may readily occur to those skilled in the art, both in vitro and in vivo tomographs, and that the basic concept of the invention may be practiced in still other forms. For example, instead of recording intensity of the received ultrasound, the time-dependent frequency sweep permits detecting and recording the effect (phase or time delay) of the ultrasound received as a function of the condition (constituency, density, etc.) of the body of the path of the ultrasound instead of attenuation. In other words, through the use of time-delay spectroscopy, the effect on ultrasound detected may be phase or time delay in the transmission of ultrasound through the body instead of attenuation. Consequently, it is intended that the claims be interpreted to cover such modifications and variations.

What is claimed is:

1. An ultrasonic system for producing a tomograph of a planar section through a body comprising means for transmitting and receiving ultrasonic energy through said body in a plurality of rectilinear scan array patterns in the plane of said section, each pattern at a different transmission angle with respect to said section, and means for detecting the attenuation of energy by said body at each raster of each pattern and means for recording in rasters the attenuation detected at each raster of the body section scanned with each recorded raster of a scan array pattern rotated by the same angle as said transmission angle.

2. An ultrasonic system as defined in claim 1 wherein said recording means is comprised of a cathode ray tube for displaying each raster of every scan pattern, and a photographic plate for recording every raster displayed, whereby a point common to a plurality of rasters in successive array patterns is recorded as the sum of attenuations for said plurality of rasters.

3. A system for producing a transillumination tomograph of a planar section through a body comprising
means for transmitting and receiving energy through a body in a plurality of rectilinear scanning array patterns in the plane of said section,
means for altering the transillumination angle of each rectilinear array pattern with respect to said body,
means for detecting the attenuation of energy by said body for each raster of said scanning patterns, and
means for adding the attenuation of each rectilinear array pattern for each raster, point by point, with attenuation data for each rectilinear array pattern superimposed to add attenuation values at common points, thereby producing a tomograph.

4. A system as defined in claim 3 including means for supporting said body in a fixed position relative to said means for transmitting and receiving energy for each rectilinear scan array pattern, and means for rotating said supporting means to a new position to alter said transillumination angle of said section for said transmitting and receiving means during each rectilinear scan array pattern.

5. A system as defined in claim 4 wherein said means for transmitting and receiving energy are comprised of ultrasonic transmitting and receiving transducers.

6. A system as defined in claim 5 wherein said means for adding attenuation of said rectilinear array patterns is comprised of a cathode ray tube for display of each raster of a rectilinear scan array pattern and a photographic plate for recording each raster, means for producing a signal proportional to the angle of rotation of said supporting means, and means responsive to said signal for rotating the relative position of each raster displayed on said cathode ray tube and said photographic plate for each rectilinear scan array pattern.

7. A system as defined in claim 6 wherein said means for rotating the relative position between each raster displayed and said photographic plate is operative to rotate each raster, and said photographic plate remains fixed in position relative to said cathode ray tube.

8. A system for producing an ultrasound transillumination tomographic image reconstruction of a planar section of a body of tissue in vitro or in vivo comprising
means for transmitting ultrasound through said body in a plurality of rectilinear scanning array patterns in the plane of said section,
means for detecting an effect by said body on ultrasound transmitted through it in each raster of each scanning array pattern, and
means for adding and recording the sum of the effect detected as a function of scanning position relative to said body for each point of said plurality of scanning array patterns to produce said tomograph image.

9. A system as defined in claim 8 including means for producing a time-dependent frequency sweep of ultrasound transmitted for each raster of each rectilinear scan array pattern comprising an ultrasonic signal generator coupled to said transmitting means to repetitively sweep said ultrasound in frequency from one frequency to another, and means for mixing the ultrasonic signal received by said receiving means with the output signal of said signal generator to produce a different frequency signal proportional to the time delay of ultrasound transmitted in a substantially straight line through said body, and a narrow bandpass filter passing said difference frequency signal for detection of said effect, thereby excluding ultrasound signals transmitted from said transmitting means to said receiving means through any longer path.

10. A system as defined in claim 9 wherein said means for transmitting and said means for detecting ultrasound are mechanically linked by means for producing movement of said transmitting means and said receiving means in parallel paths in the scanning plane for each rectilinear scan array, and said body is supported by means for holding said body in a fixed position for each rectilinear scan, including means for rotating said supporting means through an angle about an axis normal to the plane for rectilinear scan after each scan array pattern is completed.

* * * * *

UNITED STATES PATENT AND TRADEMARK OFFICE
CERTIFICATE OF CORRECTION

PATENT NO. : 4,083,232
DATED : April 11, 1978
INVENTOR(S) : Richard C. Heyser & Robert Nathan It is certified that error appears in the above-identified patent and that said Letters Patent are hereby corrected as shown below:

Column 5, line 62, change "cathode ray (CRT)" to --cathode ray tube (CRT)--

Column 6, line 57, change "is it necessary" to --it is necessary--

Column 9, line 23, change "may be" to --may use--

Signed and Sealed this

Third Day of October 1978

[SEAL]

Attest:

RUTH C. MASON
Attesting Officer

DONALD W. BANNER
Commissioner of Patents and Trademarks